United States Patent [19]

Cooper et al.

[11] Patent Number: 5,157,197
[45] Date of Patent: Oct. 20, 1992

[54] ISOPARAFFIN ALKYLATION USING A LEWIS ACID PROMOTED TRANSITION ALUMINA CATALYST

[75] Inventors: Michael D. Cooper, San Jose; David L. King, Mountain View; William A. Sanderson, Portola Valley, all of Calif.

[73] Assignee: Catalytica, Inc., Mountain View, Calif.

[21] Appl. No.: 697,318

[22] Filed: May 7, 1991

Related U.S. Application Data

[63] Continuation-in-part of Ser. No. 588,448, Sep. 26, 1990.
[51] Int. Cl.$^5$ .............................................. C07C 2/58
[52] U.S. Cl. ................................. 585/726; 585/727; 585/728
[58] Field of Search .................... 585/726, 727, 728

[56] References Cited

U.S. PATENT DOCUMENTS

| | | | |
|---|---|---|---|
| 2,748,090 | 5/1956 | Watkins | 502/203 |
| 2,804,491 | 8/1957 | May et al. | 585/726 |
| 2,824,146 | 2/1958 | Kelly et al. | 585/465 |
| 2,824,150 | 2/1958 | Knight et al. | 585/465 |
| 2,824,151 | 2/1958 | Kelly et al. | 585/465 |
| 2,824,152 | 2/1958 | Knight et al. | 585/465 |
| 2,824,153 | 2/1958 | Kelly et al. | 585/465 |
| 2,824,154 | 2/1958 | Knight et al. | 585/465 |
| 2,824,155 | 2/1958 | Knight et al. | 585/726 |
| 2,824,156 | 2/1958 | Knight et al. | 585/465 |
| 2,824,157 | 2/1958 | Knight et al. | 585/465 |
| 2,824,158 | 2/1958 | Kelly et al. | 585/465 |
| 2,824,159 | 2/1958 | Kelly et al. | 585/465 |
| 2,824,160 | 2/1958 | Knight et al. | 585/465 |
| 2,824,161 | 2/1958 | Knight et al. | 585/465 |
| 2,824,162 | 2/1958 | Knight et al. | 585/465 |
| 2,939,890 | 6/1960 | Hervert et al. | 585/467 |
| 2,945,907 | 7/1960 | Knight et al. | 585/465 |
| 2,976,338 | 3/1961 | Thomas | 585/525 |
| 3,068,301 | 12/1962 | Hervert et al. | 585/465 |
| 3,114,785 | 12/1962 | Hervert et al. | 585/669 |
| 3,131,230 | 4/1964 | Hervert et al. | 585/463 |
| 3,647,916 | 3/1972 | Caesar et al. | 585/722 |
| 3,833,679 | 9/1974 | Gardner et al. | 585/749 |
| 3,851,004 | 11/1974 | Yang | 585/467 |
| 3,855,343 | 12/1974 | Huang et al. | 585/726 |
| 3,893,942 | 7/1975 | Yang | 585/722 |
| 4,058,575 | 11/1977 | Cahn et al. | 585/374 |
| 4,308,414 | 12/1981 | Madgavkar et al. | 585/525 |
| 4,407,731 | 10/1983 | Imai | 502/203 |
| 4,427,791 | 1/1984 | Miale et al. | 502/203 |
| 4,751,341 | 6/1988 | Rodewald | 585/533 |
| 4,774,364 | 9/1988 | Chou | 585/697 |
| 4,914,256 | 4/1990 | Rodewald | 585/726 |
| 4,918,255 | 4/1990 | Chou et al. | 585/726 |
| 4,935,577 | 6/1990 | Huss, Jr. et al. | 585/726 |
| 4,956,518 | 9/1990 | Child et al. | 585/726 |
| 4,992,614 | 2/1991 | Rodewald | 585/722 |
| 4,992,616 | 2/1991 | Chou et al. | 585/722 |

FOREIGN PATENT DOCUMENTS

| | | |
|---|---|---|
| 2504121 | 10/1982 | France . |
| 0614079 | 6/1978 | U.S.S.R. . |
| WO90/00533 | 1/1990 | World Int. Prop. O. . |
| WO90/00534 | 1/1990 | World Int. Prop. O. . |

OTHER PUBLICATIONS

Yagubov, Kh. M. et al., *Azerb Khim. Zh.,* (1984) 5:58.
Kozorezov, Yu et al., *Zh. Prikl. Khim.* (Leingrad), (1984) 57(12):2681-4.
Kozorezov, Yu, et al., *Neftekhimiya.* (1979) 19(3):385-9.
Hutson, Jr., T., et al., *Hydrocarbon Processing* (1975) pp.107-110.
Kozorezov, Yu. I., *Neftekhimiya* (1977) 17(3):396-400; abstract only.
K. Matsuura et al., "Catalytic Properties of BF$_3$-treated Aluminas", in *Journal of Catalysis* (1971) 23:395-7.
K. Matsurra et al., "Catalytic Properties of BF$_3$-treated Aluminas", in *Bull. of the Chem. Soc. of Japan* (1972) 45:2079-83.
K. Matsuura et al., "Catalytic Properties of BF$_3$-treated Aluminas", in *Journal of Catalysis* (1972) 26:127-34.

*Primary Examiner*—Patrick P. Garvin
*Assistant Examiner*—E. D. Irzinski
*Attorney, Agent, or Firm*—Morrison & Foerster

[57] ABSTRACT

This invention is a process for the alkylation of isoparaffin with olefins using a catalyst system comprising certain transition aluminas promoted with a Lewis acid (preferably BF$_3$), and free Lewis acid. The product alkylate is a complex mixture of branched paraffins suitable for use as a high octane blending component for motor fuels.

20 Claims, 1 Drawing Sheet

ISOPARAFFIN ALKYLATION USING A LEWIS ACID PROMOTED TRANSITION ALUMINA CATALYST

RELATED APPLICATIONS

This is a continuation-in-part of U.S. patent application Ser. No. 07/588,448 filed Sep. 26, 1990, the entirety of which is incorporated by reference.

FIELD OF THE INVENTION

This invention is a process for the alkylation of isoparaffin with olefins using a catalyst system comprising certain transition aluminas promoted with a Lewis acid (preferably $BF_3$) and free Lewis acid. The product alkylate is a complex mixture of branched paraffins suitable for use as a high octane blending component for motor fuels.

BACKGROUND OF THE INVENTION

The preparation of high octane blending components for motor fuels using strong acid alkylation processes (notably where the acid is hydrofluoric acid or sulfuric acid) is well-known. Alkylation is the reaction in which an alkyl group is added to an organic molecule, typically an aromatic or olefin. For production of gasoline blending stocks, the reaction is between an isoparaffin and an olefin. Alkylation processes have been in wide use since World War II when high octane gasolines were needed to satisfy demands from high compression ratio or supercharged aircraft engines. The early alkylation units were built in conjunction with fluid catalytic cracking units to take advantage of the light end by-products of the cracking units: isoparaffins and olefins. Fluidized catalytic cracking units still constitute the major source of feedstocks for gasoline alkylation units. In spite of the mature state of strong acid alkylation technology, existing problems with the hydrofluoric and sulfuric acid technologies continue to be severe: disposal of the used acid, unintentional emission of the acids during use or storage, substantial corrosivity of the acid catalyst systems, and other environmental concerns.

Although a practical alkylation process using solid acid catalysts having little or no corrosive components has long been a goal, commercially viable processes do not exist.

The open literature shows several systems used to alkylate various hydrocarbon feedstocks.

The American Oil Company obtained a series of patents in the mid-1950's on alkylation processes involving $C_2$-$C_{12}$ (preferably $C_2$ or $C_3$) olefins and $C_4$-$C_8$ isoparaffins. The catalysts used were $BF_3$-treated solids and the catalyst system (as used in the alkylation process) also contained free $BF_3$. A summary of those patents is found in the following list:

| U.S. Pat. No. | Inventor | $BF_3$-Treated Catalyst* (with free $BF_3$) |
|---|---|---|
| 2,804,491 | Kelly et al. | $SiO_2$ stabilized $Al_2O_3$(10%-60% by weight $BF_3$) |
| 2,824,146 | Kelly et al. | metal pyrophosphate hydrate |
| 2,824,150 | Knight et al. | metal sulfate hydrate |
| 2,824,151 | Kelly et al. | metal stannate hydrate |
| 2,824,152 | Knight et al. | metal silicate hydrate |
| 2,824,153 | Kelly et al. | metal orthophosphate hydrate |
| 2,824,154 | Knight et al. | metal tripolyphosphate hydrate |
| 2,824,155 | Knight et al. | metal pyroarsenate hydrate |
| 2,824,156 | Kelly et al. | Co or Mg arsenate hydrate |
| 2,824,157 | Knight et al. | Co, Al, or Ni borate hydrate |
| 2,824,158 | Kelly et al. | metal pyroantimonate hydrate salt |
| 2,824,159 | Kelly et al. | Co or Fe molybdate hydrate |
| 2,824,160 | Knight et al. | Al, Co, or Ni tungstate hydrate |
| 2,824,161 | Knight et al. | borotungstic acid hydrate or Ni or Cd borotungstate hydrate |
| 2,824,162 | Knight et al. | phosphomolybdic acid hydrate |
| 2,945,907 | Knight et al. | solid gel alumina (5%-100% by weight of Zn or Cu fluoborate, preferably anhydrous) |

*may be supported on $Al_2O_3$

None of these disclose a process for alkylating olefins and isoparaffins using neat alumina treated with $BF_3$.

Related catalysts have been used to oligomerize olefins. U.S. Pat. No. 2,748,090 to Watkins suggests the use of a catalyst made up of a Group VIII metal (preferably nickel), a phosphoric acid (preferably containing phosphorus pentoxide), placed on an alumina adsorbent, and pretreated with $BF_3$. Alkylation of aromatics is suggested.

U.S. Pat. No. 2,976,338 to Thomas suggests a polymerization catalyst comprising a complex of $BF_3$ or $H_3PO_4$ optionally on an adsorbent (such as activated carbon) or a molecular sieve optionally containing potassium acid fluoride.

Certain references suggest the use of alumina-containing catalysts for alkylation of aromatic compounds. U.S. Pat. No. 3,068,301 to Hervert et al. suggests a catalyst for alkylating aromatics using "olefin-acting compounds". The catalyst is a solid, silica-stabilized alumina up to 10% $SiO_2$, all of which has been modified with up to 100% of weight $BF_3$. None of the prior references suggest a process nor the material used in the processes disclosed here.

Other $BF_3$-treated aluminas are known. For instance, U.S. Pat. No. 3,114,785 to Hervert et al. suggests the use of a $BF_3$-modified substantially anhydrous alumina to shift the double bond of 1-butene to produce 2-butene. The preferred alumina is substantially anhydrous gamma-alumina, eta-alumina, or theta-alumina. The various aluminas will adsorb or complex with up to about 19% by weight fluorine depending upon the type of alumina and the temperature of treatment. Hervert et al. does not suggest using these catalysts in alkylation reactions.

In U.S. Pat. No. 4,407,731 to Imai, a high surface area metal oxide such as alumina (particularly gamma-alumina, eta-alumina, theta-alumina, silica, or a silica-alumina) is used as a base or support for $BF_3$. The $BF_3$ treated metal oxide is used for generic oligomerization and alkylation reactions. The metal oxide is treated in a complicated fashion prior to being treated with $BF_3$. The first step entails treating the metal oxide with an acid solution and with a basic aqueous solution. The support is washed with an aqueous decomposable salt such as ammonium nitrate. The support is washed using deionized $H_2O$ until the wash water shows no alkali or alkaline earth metal cations in the filtrate. The support is dried and calcined. The disclosure suggests generically that $BF_3$ is then introduced to the treated metal oxide support. The examples show introduction of the $BF_3$ at elevated temperature, e.g., 300° C. or 350° C.

Similarly, U.S. Pat. No. 4,427,791 to Miale et al. suggests the enhancement of the acid catalytic activity of inorganic oxide materials (such as alumina or gallia) by contacting the material with ammonium fluoride or boron fluoride, contacting the treated inorganic oxide with an aqueous ammonium hydroxide or salt solution, and calcining the resulting material. The inorganic oxides treated in this way are said to exhibit enhanced Brönsted acidity and, therefore, is said to have improved acid activity towards the catalysis of numerous and several reactions (such as alkylation and isomerization of various hydrocarbon compounds). A specific suggested use for the treated inorganic oxide is as a matrix or support for various zeolite materials ultimately used in acid catalyzed organic compound conversion processes.

U.S. Pat. No. 4,751,341 to Rodewald shows a process for treating a ZSM-5 type zeolite with $BF_3$ to reduce its pore size, enhance its shape selectivity, and increase its activity towards the reaction of oligomerizing olefins. The patent also suggests using these materials for alkylation of aromatic compounds.

Certain Soviet publications suggest the use of $Al_2O_3$ catalysts for alkylation processes. Benzene alkylation using those catalysts (with 3 ppm to 5 ppm water and periodic additions of $BF_3$) is shown in Yagubov, Kh. M. et al., *Azerb. Khim. Zh.*, 1984, (5) p. 58. Similarly, Kozorezov, Yu and Levitskii, E. A., *Zh. Print. Khim.* (Leningrad), 1984, 57 (12), p. 2681, show the use of alumina which has been treated at relatively high temperatures and modified with $BF_3$ at 100° C. There are no indications that $BF_3$ is maintained in excess. Isobutane alkylation using $Al_2O_3/BF_3$ catalysts is suggested in *Neftekhimiya*, 1977, 17 (3), p. 396; 1979, 19 (3), P. 385. The olefin is ethylene. There is no indication that $BF_3$ is maintained in excess during the reaction. The crystalline form of the alumina is not described.

U.S. Pat. No. 4,918,255 to Chou et al. suggests a process for the alkylation of isoparaffins and olefins using a composite described as "comprising a Lewis acid and a large pore zeolite and/or a non-zeolitic inorganic oxide". The process disclosed requires isomerization of the olefin feed to reduce substantially the content of alpha-olefin and further suggests that water addition to the alkylation process improves the operation of the process. The best Research Octane Number (RON) product made using the inorganic oxides (in particular $SiO_2$) is shown in Table 6 to be 94.0.

U.S. Pat. No. 4,992,616 to Chou et al. deals with the process noted above for alkylation of isoparaffins and olefins using a composite described as "comprising a Lewis acid and a large pore zeolite" but requiring water addition for improvement the operation of the process. The best Research Octane Number (RON) product shown in the examples and made using the disclosed invention is 86.0 (Table 2).

U.S. Pat. No. 4,956,518 to Chow et al. shows an alkylation process using a number of catalysts including one of silica/$BF_3$. The process also requires the addition of controlled amounts of water. The best RON (Table 3) is shown to be 97.2.

Similarly, PCT published applications WO 90/00533 and 90/00534 (which are based in part on the U.S. patent to Chou et al. noted above) suggest the same process as does Chou et al. WO 90/00534 is specific to a process using boron trifluoride-treated inorganic oxides including "alumina, silica, boria, oxides of phosphorus, titanium oxide, zirconium oxide, chromia, zinc oxide, magnesia, calcium oxide, silica-alumina-zirconia, chromia-alumina, alumina-boria, silica-zirconia, and the various naturally occurring inorganic oxides of various states of purity such as bauxite, clay and diatomaceous earth". Of special note is the statement that the "preferred inorganic oxides are amorphous silicon dioxide and aluminum oxide". The examples show the use of amorphous silica (and $BF_3$) to produce alkylates having an RON of no greater than 94.

Similarly, U.S. Pat. No. 4,935,577 to Huss, Jr. et al. teaches a process for the catalytic distillation of various hydrocarbons by, e.g., alkylation or oligomerization, using a catalyst "consisting essentially of a Lewis acid promoted inorganic oxide". The inorganic oxide may be selected from the non-zeolitic materials discussed above with regard to the Chou et al. published PCT applications. Additionally, the inorganic oxide may be a large pore crystalline molecular sieve. The best exemplified alkylate appeared to have an RON value of 93 (Table 2).

None of these disclosures show the alkylation of isoparaffins and olefins using crystalline transition aluminas promoted with Lewis acids for the production of high octane gasoline blending components.

SUMMARY OF THE INVENTION

Figure 1:
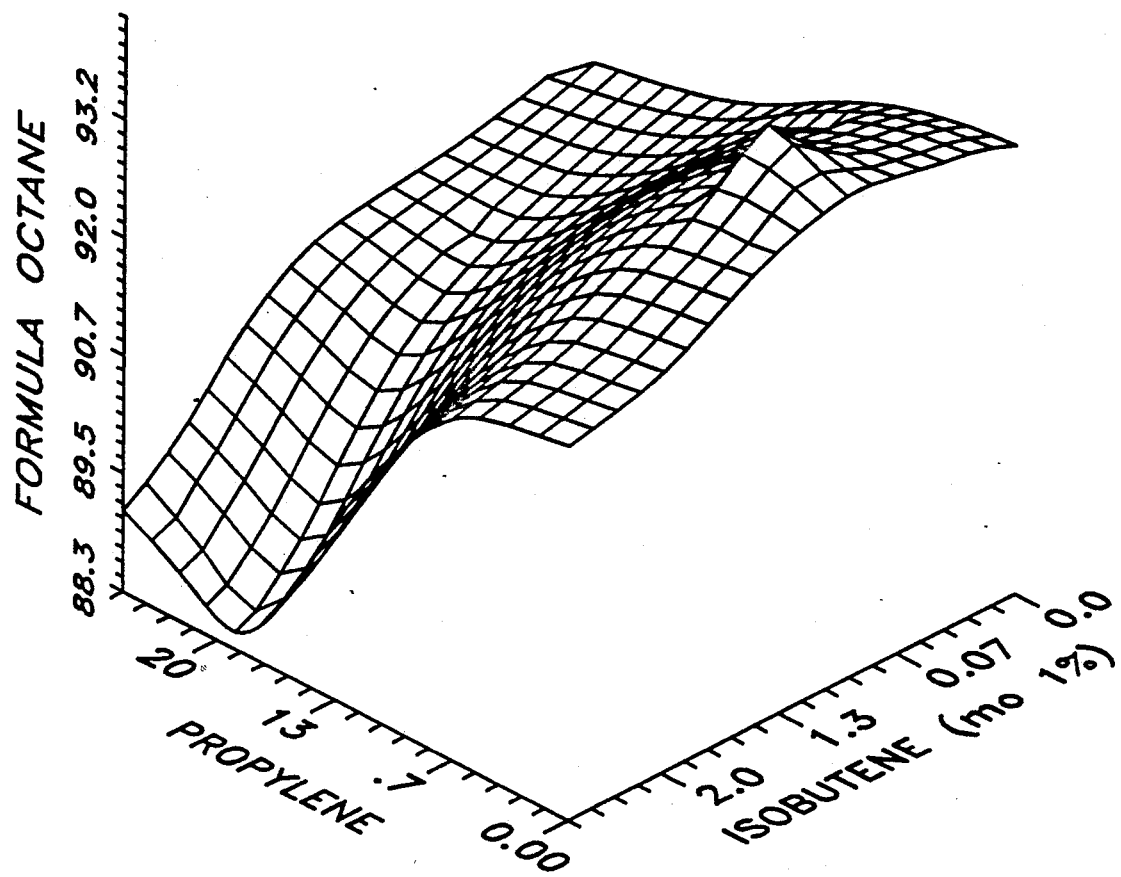
FIG. 1 is a three-dimensional graph showing octane sensitivity for the inventive process as a function of olefin feed content.

This invention is a process for producing alkylates suitable for use as blending components in motor fuels. The alkylates are produced from olefins and isoparaffins. The catalyst used is selected from one or more transitional aluminas which are treated with one or more Lewis acids, preferably $BF_3$. The process optimally utilizes a minor amount of free Lewis acid.

Use of this catalyst system produces high octane alkylate at a variety of reaction temperatures between $-30°$ C. and 40° C. The catalyst's high activity can result in low operating costs because of its ability to operate at high space velocities.

Treatment of the transition aluminas with one or more Lewis acids (either prior to its introduction into the alkylation reactor or in situ) as described here imparts a change to the chemical properties of the alumina in that the alumina retains an amount of the Lewis acid even after the activity of the catalyst system slows to a non-economic level.

DESCRIPTION OF THE INVENTION

This invention is a process for producing alkylate products from olefins and isoparaffins by using Lewis acid treated aluminas as catalysts. The process uses a minor amount of free Lewis acid.

The novel catalyst of this invention is made by contacting free Lewis acid with certain transition alumina substrates.

The Catalyst

The catalyst comprises or consists essentially of a major amount of transition aluminas (preferably eta- or gamma-alumina) which has been treated with a Lewis acid, preferably $BF_3$. The catalyst is acidic in nature and contains substantially no metals (except, of course, aluminum and the semi-metal boron) in catalytic amounts except as may be present in trace amounts in the $BF_3$ or alumina.

Alumina

Aluminum oxide (alumina) occurs abundantly in nature, usually in the form of a hydroxide in the mineral bauxite, along with other oxidic impurities such as $TiO_2$, $Fe_2O_3$, and $SiO_2$. The Bayer process is used to produce a reasonably pure $Al_2O_3$ having a minor amount of $Na_2O$. The Bayer process $Al_2O_3$ is further treated to produce a variety of alumina hydroxides:

| Material | Common Name | % $H_2O$ | $H_2O/Al_2O_3$ | CAS Index No. |
| --- | --- | --- | --- | --- |
| α-trihydrate | hydrargillite/gibbsite | 35 | 3.0 | 14762-493 |
| β-trihydrate | bayerite | 35 | 3.0 | 20257-20-9 or 12252-72-1 |
| β-trihydrate | nordstrandite | 35 | 3.0 | 13840-05-6 |
| α-monohydrate | boehmite | 15 | 1.0 | 1318-23-6 |
| hydrate | psuedoboehmite | 26 | 2.0 | — |

The aluminum hydroxides may then be treated by heating to produce various activated or transition aluminas. For instance, the aluminum hydroxide known as boehmite may be heated to form a sequence of transition phase aluminas: gamma, delta, theta, and finally, alpha (see Wefers et al., "Oxides and Hydroxides of Alumina", Technical Paper No. 19, Aluminum Company of America, Pittsburgh Transition aluminas (and their crystalline forms) include:

| | |
| --- | --- |
| gamma | tetragonal |
| delta | orthorhombic/tetragonal |
| eta | cubic |
| theta | monoclinic |
| chi | cubic/hexagonal |
| kappa | hexagonal |
| lambda | orthorhombic |

Activated aluminas and aluminum hydroxides are used in various chemical processes as catalyst and adsorbents.

The aluminas suitable for use in this process include the noted transition aluminas: gamma, delta, eta, theta, chi, kappa, or lambda. Especially preferred are gamma- and eta-aluminas. Mixtures of the two are also desireable.

Since it is difficult to produce a substantially pure single phase transition alumina, mixtures of various aluminas are tolerable so long as a major amount of the specified alumina is present in the catalyst. For instance, in the production of eta-alumina, gamma-alumina is often concurrently present in the resulting product. Indeed, x-ray diffraction analysis can only difficulty detect the difference between the two phases. Alumnium hydroxides (boehmite, gibbsite, etc.) may be present in the predominately transition phase product in more than trivial amounts so long as they do not substantially affect the desired alkylation reaction.

The alumina may be produced in any appropriate form such as pellet, granules, bead, sphere, powder, or other shape to facilitate its use in fixed beds, moving beds, or fluidized beds.

Lewis Acids

The catalyst used in this process uses one or more Lewis acids in conjunction with the alumina noted above.

A Lewis acid is a molecule which can form another molecule or an ion by forming a complex in which it accepts two electrons from a second molecule or ion. Typical strong Lewis acids include boron halides such as $BF_3$, $BCl_3$, $BBr_3$, and $BI_3$; antimony pentachloride ($SbF_5$); aluminum halides ($AlCl_3$ and $AlBr_3$); titanium halides such as $TiBr_4$, $TiCl_4$, and $TiCl_3$; zirconium tetrachloride ($ZrCl_4$); phosphorus pentafluoride ($PF_5$); iron halides such as $FeCl_3$ and $FeBr_3$; and the like. Weaker Lewis acids such as tin, indium, bismuth, zinc, or mercury halides are also acceptable. Preferred Lewis acids are $SbF_5$, $AlCl_3$, and $BF_3$; most preferred is $BF_3$.

Catalyst Preparation

The catalyst may be prepared in situ in the alkylation reactor by passing the Lewis acid in gaseous form through the vessel containing the transition alumina. Alternatively, the alumina may be contacted with the Lewis acid and later introduced into the reactor. In any case, the alumina must be substantially dry prior to contact with the Lewis acid and maintained at a very low free $H_2O$ water content. Contact temperatures between −25° C. and about 100° C. are acceptable; a temperature between −25° C. and 30° C. is preferred. The partial pressure of gaseous Lewis acid added to the alumina is not particularly important so long as a sufficient amount of Lewis acid is added to the alumina. We have found that treatment of the alumina with $BF_3$ at the noted temperatures will result in an alumina-$BF_3$ complex containing $BF_3$ sufficient to carry out the alkylation. The alumina contains between 0.5% and 30% by weight of $BF_3$.

Obviously, the alumina may be incorporated into a binder prior to its treatment with Lewis acid. The binders may be clays (such as montmorillonite and kaolin) or silica based materials (such as gels or other gelatinous precipitates). Other binder materials include carbon and metal oxides such as alumina, silica, titania, zirconia, and mixtures of those metal oxides. The composition of the binders is not particularly critical but care must be taken that they not substantially interfere with the operation of the alkylation reaction.

The preferred method for incorporating the catalytic alumina into the binder is by mixing an aluminum hydroxide precursor (such as boehmite) with the binder precursor, forming the desired shape, and calcining at a temperature which both converts the aluminum hydroxide precursor into the appropriate transition phase and causes the binder precursor to bind the alumina particles. The absolute upper temperature limit for this calcination is about 1150° C. Temperatures below about 1000° C. are appropriate.

Because of the desirability of using a slurry reactor and maximizing surface area, the most desired form of the catalyst is a powder of neat transition alumina sized appropriately for the slurry reactor system employed.

Process

The alkylation process involves contacting an isoparaffin with an olefin in the presence of the catalyst discussed above and in the presence of a minor amount of free Lewis acid.

Specifically, the catalyst of this invention is active at low temperatures (as low as −30° C.) as well as at higher temperatures (nearing 50° C.). Lower temperatures (−5° C. to 15° C.) are preferred because of the enhanced octane of the alkylate produced and are particularly preferred if the feedstream contains more than about 1% isobutylene. Higher temperatures also tend to produce larger amounts of polymeric materials.

The pressure used in this process is not particularly critical. In general, the pressure must be kept high enough to maintain the reactants and products in the liquid phase, although the catalyst will produce alkylation products when the feedstock is gaseous. As a practical guideline, the process may be operated at atmospheric pressure to about 750 psig. Higher pressures within the range allow recovery of excess reactants by flashing after the product stream leaves the alkylation reactor.

The amount of catalyst used in this process depends upon a wide variety of disparate variables. Nevertheless, we have found that the Weight Hourly Space Velocity ("WHSV"=weight of olefin feed/hour÷weight of catalyst) may effectively be between 0.1 and 120, especially between 0.5 and 30. The overall molar ratio of paraffin to olefin is between about 1.0 and 50.0. Preferred ranges include 2.0 and 25.0; the more preferred include 3.0 and 12.0.

The feedstreams introduced into the catalyst are desirably chiefly isoparaffins having from four to ten carbon atoms and, most preferably, four to six carbon atoms. Isobutane is most preferred because of its ability to make high octane alkylate. The olefins desirably contain from three to five carbon atoms, i.e., propylene, cis- and trans-butene-2, butene-1, and amylenes. Preferably, the olefin stream contains little (if any) isobutylene. Similarly, for the inventive catalysts, the process works better in producing high octane alkylate if the feedstream contains little or no butadiene (preferably less than 0.2% to 0.3% molar of the total feedstream) and a minimal amount of isobutylene, e.g., less than about 2.5% molar. Similarly the butene-1 content should be minimized.

The products of this alkylation process typically contain a complex mixture of highly branched alkanes. For instance, when using isobutane as the alkane and n-butylene as the olefin, a mixture of 2,2,3-; 2,2,4-; 2,3,3-; and 2,3,4-trimethylpentane (TMP) will result often with minor amounts of other isomeric or polymeric products. The 2,3,4-TMP isomer is the lowest octane isomer of the noted set. The 2,2,3- and 2,2,4-TMP isomers are higher octane components. Calculated average octane values (RON plus Motor Octane Number/2) of the various $C_8$ isomers are:

| Isomer | Octane (R + M)/2 |
|--------|------------------|
| 2,2,3- | 104.80 |
| 2,2,4- | 100.00 |
| 2,3,3- | 102.08 |
| 2,3,4- | 99.3 |

Clearly an alkylation process using the noted feedstocks should maximize $C_8$ production, minimize the 2,3,4-TMP isomer, $C_7$ isomers, and $C_{12}+$ fraction while maximizing 2,2,3- and 2,3,3-TMP isomers.

The process (in addition to being capable of sustaining the temperatures noted above) can be carried out in the liquid, vapor, or mixed liquid and vapor phase. Liquid phase operation is preferred in this process.

The process involved may utilize the catalyst in a fixed bed using single or multiple feeds. That is to say, the feedstocks may be independently introduced at one or more points throughout the bed or between multiple beds. Desirably, the catalyst is contacted with the feedstocks in one or more of continuously stirred reactors, preferably with feed to each reactor.

We have found that addition of water or alcohols to the alkylation step does not produce improvement in the alkylate produced.

The invention has been disclosed by direct description. Below may be found a number of examples showing various aspects of the invention. The examples are only examples of the invention and are not to be used to limit the scope of the invention in any way.

EXAMPLES

Example 1: Catalyst Screening

This example shows the preparation of a number of alumina-based catalysts in situ and their subsequent use in an alkylation reaction using model feeds. It is used to evaluate catalyst activity and selectivity.

The alumina samples were dried at 150° C. overnight and charged to a semi-batch reactor having an internal volume of about 500 cc. The reactor temperature was controllable over the range of $-5°$ C. to 40° C. For initial catalyst treatment, the reactor containing the catalyst was purged with an inert gas and cooled to about 0° C. About 275 cc of isobutane was added to the reactor. After a brief degassing, $BF_3$ was added batchwise. After $BF_3$ is added, the pressure typically drops as the alumina adsorbs or reacts with the $BF_3$. Additional infusions of $BF_3$ are made until the pressure in the reactor no longer drops. The $BF_3$ saturation equilibrium pressure was about 40 psig. The liquid phase concentration of $BF_3$ was about 1.5%. At that point the alumina had adsorbed or reacted with all of the $BF_3$ possible at that temperature and the catalyst was in its most active form.

A 4/1 molar mixture of isobutane and trans-2-butene was added to the reactor at a WHSV of 3.5 until the paraffin to olefin ratio reached 25.

The product alkylate was then removed from the reactor vessel and analyzed using gas-liquid chromatography.

The results of those runs are shown in Table I.

TABLE 1

| Alumina Type | Surface Area | % $C_8$ in Alkylate Product |
|--------------|--------------|------------------------------|
| gamma | 180 m²/gm | 95.4 |
| gamma | 116 m²/gm | 82.07 |
| delta | 118 m²/gm | 94.3 |
| pseudoboehmite | 352 m²/gm | 74.2 |
| bayerite | 40 m²/gm | 69.1 |
| pseudoboehmite | 250 m²/gm | 59.6 |
| boehmite | 150 m²/gm | 59.8 |

It is clear from these preliminary screening data that the transition (gamma and delta) aluminas produce significantly higher percentages of $C_8$ in the product alkylate than do the other aluminum hydroxide catalysts. The result did not appear to correlate to the specific surface area of the catalyst.

Example 2: Catalyst Screening

This example compares the performance of eta-alumina (a preferred from of the inventive catalyst) with representative samples of other acidic oxides each combined with $BF_3$ for the reaction of isobutane with butenes to produce alkylate.

The eta-alumina sample was prepared by a controlled thermal treatment of bayerite (Versal B from LaRoche Chemical) for 15 hours at 250° C. and 24 hours at 500° C. under a $N_2$ atmosphere.

The comparative oxidic materials were: silica-alumina, synthetic mordenite zeolite, and fumed silica. The silica-alumina (obtained from Davison Chemical) contained 86.5% $SiO_2$ and had a surface area of 392 $m^2/gm$. It was used without further treatment.

The mordenite was a hydrogen form zeolite and was obtained from Toyo Soda. It was prepared from Na-mordenite and subjected to ion exchange, steam treatment, and calcination to achieve a Si/Al ratio of 28.

Each of the samples was dried at 150° C. overnight and introduced into the semi-batch reactor described in Example 1. The samples were purged with a dry inert gas and cooled to 0° C. Isobutane was added to the reactor to an initial volume of 100 cc. $BF_3$ was added with stirring until an equilibrium pressure of 30 psig was obtained.

A mixture of isobutane/t-2-butene was fed to the reactor. At the completion of the reaction, alkylate was removed and analyzed by gas-liquid chromatography. The RON were calculated from the gas-liquid chromatography data using the well-known correlations in Hutson and Logan, "Estimate Alky Yield and Quality", Hydrocarbon Processing, September, 1975, pp. 107–108. The summary of the experiments and results is shown in the table below:

TABLE 2

|  | Eta-$Al_2O_3$ | Silica-Alumina | Dealuminated Mordenite | Silica |
|---|---|---|---|---|
| Catalyst charge (g) | 3.5 | 3.7 | 2.4 | 1.8 |
| Temperature (°C.) | 0 | 0 | 0 | 0 |
| i-$C_4$ charge ml (initial) | 180 | 180 | 180 | 375 |
| i-$C_4/C_4^=$ feed ratio (molar) | 5.2 | 5.9 | 5.9 | 9.5 |
| Space velocity (WHSV) | 2.6 | 2.0 | 3.3 | 2.8 |
| Run time (minutes) | 36 | 34 | 28 | 58 |
| i-$C_4/C_4^=$ (final) | 23.5 | 30.3 | 34.0 | 57 |
| Butene conversion (%) | 100 | 100 | 100 | 100 |
| Product analysis (weight %): |  |  |  |  |
| $C_5$-$C_7$ | 3.1 | 5.2 | 11.3 | 13.0 |
| $C_8$ saturates | 95.7 | 75.8 | 71.7 | 70.9 |
| $C_9^+$ | 1.2 | 19.0 | 17.0 | 16.1 |
| TMP/$C_8$ total (%) | 93.0 | 91.2 | 91.3 | 91.6 |
| Yield (w/w) | 2.08 | 1.55 | 0.99 | 1.43 |
| RON | 99.3 | 94.6 | 93.0 | 93.0* |
| Octane (R + M/2) | 97.9 | 93.1 | 92.0 | 92.1* |

*estimated

Clearly, for the eta-alumina catalyst, the yield of $C_8$'s was significantly higher; the overall yield and RON were much better.

EXAMPLE 3

This example shows that the addition of either water or methanol produces no appreciable improvement on the alkylation of butene-2 with isobutane using the inventive alumina catalyst. Indeed, water and methanol appear to be detrimental.

Three separate semi-batch reactors were dried and flushed with nitrogen. A sample of 2.5 gm of a gamma-alumina (LaRoche VGL) was loaded into each bottle. The alumina samples had been previously dried at 110° C. overnight. An amount of 0.278 gms of deionized water was added dropwise to one reactor. An amount of 0.988 gms of methanol was added to another reactor. These amounts were calculated to be 10% of the catalyst plus water equivalent. The remaining reactor was used as a control reactor. Isobutane (246 cc) was added to each bottle; $BF_3$ was added (with stirring) until the pressure reached a constant 30 psig. A feedstock of 2/1: isobutane/2-butene was continuously added at a rate of 1.6 cc/minute. The reaction continued for about 75 minutes after which samples of the reactor liquids were extracted and analyzed using a gas-liquid chromatograph. The conversion of olefin was more than 99% in each case. Other reaction conditions and a summary of reaction results are shown in the following table:

|  | Alumina | Alumina w/$H_2O$ | Alumina w/$CH_3OH$ |
|---|---|---|---|
| Reaction Conditions |  |  |  |
| Reaction temperature (°C.) | 0 | 0 | 0 |
| Pressure (psig) | 30.0 | 30.0 | 30.0 |
| WHSV | 5.653 | 5.526 | 5.526 |
| I/O (w/w) | 10.33 | 10.63 | 10.63 |
| Product |  |  |  |
| $C_5$-$C_7$ | 2.29% | 2.80% | 14.85% |
| $C_8$ (saturated) | 94.61% | 89.81% | 64.67% |
| $C_{12}$ | 2.52% | 6.81% | 13.58% |
| TMP/$C_8$ | 98.74% | 98.83% | 96.18% |
| Yield (w/w) | 2.19 | 2.14 | 1.87 |
| RON | 100.05 | 98.19 | 93.49 |
| R + M/2 | 98.32 | 96.06 | 92.74 |

It is clear that neither water nor methanol created any advantage in the operation of the process in producing a gasoline alkylate. The gross amounts of $C_8$ produced were smaller than for the inventive alumina; the amount of undesirable $C_{12}^+$ were two to four times higher than for the inventive alumina. The yields were lower and, probably most importantly, the octane values of the comparative products were significantly lower.

EXAMPLE 4

This example shows the suitability of the inventive catalyst (gamma-alumina, LaRoche GL) for a variety of olefin feedstocks. The following reaction conditions were used for the test series:

| Temperature | 0° C. |
|---|---|
| Total pressure | 30 psig |
| WHSV | 4 |

A semi-batch reactor was utilized in each run.

The olefin feedstocks were mixtures which were chosen to allow us to identify desireable and undesireable combinations of feed materials. The mixtures were:

| Mixture No. | 1-$C_4^=$ | 1-$C_4^=$ | $C_3^=$ | 60/40 mixture of cis/trans 2-$C_4^=$ |
|---|---|---|---|---|
| 1 | 25 | 25 | 20 | 30 |
| 2 | 10 | 25 | 20 | 45 |
| 3 | 25 | 10 | 20 | 45 |
| 4 | 10 | 10 | 20 | 60 |
| 5 | 25 | 25 | 05 | 45 |
| 6 | 10 | 25 | 05 | 60 |
| 7 | 25 | 10 | 05 | 60 |
| 8 | 10 | 10 | 05 | 75 |

The products made were analyzed using gas-liquid chromatography and their respective octane numbers calculated as follows:

| Mixture No. | $C_5$-$C_7$ | $C_8$ | $C_{12}^+$ | TMP/$C_8$ | RON | R + M/2 |
|---|---|---|---|---|---|---|
| 1 | 14.4 | 55.0 | 23.7 | 94.1 | 86.3 | 86.3 |
| 2 | 15.3 | 52.9 | 25.9 | 93.6 | 86.3 | 87.1 |
| 3 | 15.4 | 58.6 | 20.2 | 94.9 | 88.7 | 87.9 |
| 4 | 14.5 | 60.8 | 17.0 | 95.1 | 90.9 | 90.1 |
| 5 | 10.2 | 66.4 | 17.9 | 92.6 | 89.9 | 88.9 |
| 6 | 7.3 | 63.9 | 25.3 | 95.1 | 89.8 | 89.0 |
| 7 | 6.4 | 74.9 | 16.1 | 94.7 | 92.1 | 90.5 |
| 8 | 6.8 | 71.9 | 11.6 | 96.3 | 93.1 | 91.9 |

These data show that increases in isobutene and propylene feed concentrations directionally cause the inventive alkylation process to produce lower alkylate $C_8$ content. As shown in FIG. 1, smaller amounts of either $C_3^=$ or i-$C_4^=$ cause no more harm to alkylate quality but are generally undesirable if extremely high octane alkylates are necessary.

EXAMPLE 5

This example demonstrates the performance of the transition alumina/$BF_3$ catalysts in reacting isobutance with butenes to form high octane product under conditions of high space velocity and low paraffin/olefin feed ratios.

A sample of gamma-alumina (VGL, LaRoche) was dried overnight at 110° C. and loaded into the semi-continuous reactor unit described in Example 1. The catalyst was purged with dry inert gas and cooled to 0° C. Isobutane was added to the reactor and then the system was exposed to $BF_3$ under stirring conditions until an equilibrium pressure of 30 psig was achieved. A feed comprising pure trans-2-butene was then pumped into the reactor under vigorous stirring conditions over a period of 60 minutes; samples were obtained periodically during the run. The results are summarized in the table below:

| Catalyst charge (g) | 2.5 | |
|---|---|---|
| Temperature (°C.) | 0 | |
| i-$C_4$ charge ml | 300 | |
| Olefin feed | Trans-2-butene | |
| Space velocity (WHSV) | 26.4 | |
| Run time (minutes) | 30 | 30 |
| Equivalent external i-$C_4$/$C_4^=$ | 5.4 | 2.6 |
| Butene converstion (%) | 100 | 100 |
| Product analysis (weight %): | | |
| $C_5$-$C_7$ | 3.2 | 4.7 |
| $C_8$ saturates | 91.1 | 81.9 |
| $C_9^+$ | 5.7 | 13.4 |
| TMP/$C_8$ total (%) | 97.6 | 96.6 |
| RON | 99.0 | 96.8 |
| Octane, R + M/2 | 97.0 | 95.3 |

EXAMPLE 6

This example shows the utility of the catalyst system on a feed obtained from a refinery MTBE unit. The feed, containing minor amounts of butadiene and isobutene, was introduced into a bed of a commercial hydroisomerization catalyst (0.3% Pd on $Al_2O_3$) at 400 cc/hr, 80° C., and 350 psig along with 14 sccm $H_2$. The molar ratio of $H_2$:butadiene was 6:1. The thusly treated feed, containing no butadiene and only 1.53% (molar) of isobutene, was mixed with an appropriate amount of isobutane. The mixture had the following approximate composition:

| Component | mole % |
|---|---|
| propylene | 0.02 |
| propane | 0.13 |
| isobutane | 80.14 |
| isobutene | 0.52 |
| 1-butene | 0.75 |
| butadiene | — |
| n-butane | 3.84 |
| t-butene-2 | 8.23 |
| c-butene-2 | 4.05 |
| 3-methyl-1-butene | 0.01 |
| isopentane | 1.73 |
| 1-pentene | 0.01 |
| 2-methyl-1-butene | 0.03 |
| n-pentane | 0.08 |
| t-2-pentene | 0.18 |
| c-2-pentene | 0.06 |
| 2-methyl-2-butene | 0.23 |

This mixture had a paraffin/olefin ratio of 6.10 and an isobutane/olefin ratio of 5.69.

The mixture was then admitted to a pair of continuous laboratory reactors each containing 280 cc of liquid and containing 5.04 g of catalyst. The temperature was maintained at 0° F. The WHSV for the reactor was 4.3 hr$^{-1}$ and the LHSV was 1.07 hr$^{-1}$. The catalyst was a gamma alumina (LaRoche VGL) and was prepared by adding the proper amount to the reactors along with a small amount of isobutane, pressuring the reactor to about 40 psig of $BF_3$, and maintaining that pressure for the duration of the test.

The test was run for 41 hours total time. The catalyst was regenerated four times during the run by rinsing the catalyst in 200 cc of trimethyl pentane, heating to 150° C. in air for 45 minutes to volatilize a portion of the reaction product on the catalyst, and heating the catalyst to 600° C. in air for 60 minutes to oxidize the remaining hydrocarbonaceous materials. Small amounts of the catalyst were added as necessary with the regenerated catalyst to restore the catalyst to its proper amount upon return to the reactor (0.41 g @ cycle 2, 0.97 g @ cycle 3, 0.0 g @ cycle 4, and 0.47 g @ cycle 5). About 4.5 liters (3.2 kg) of stripped $C_{5+}$ alkylate was collected having about 7.6% $C_{5-7}$, 81.2% $C_8$, 4.4% $C_{9-11}$, and 6.8% $C_{12}$ (all by weight). Using the Hutson method discussed above, the octanes were calculated to be: RON=96.6, MON=93.3, and the (R+M)/2=94.95. The product was then engine-tested using API methodology and the octanes were measured to be: RON=98.7, MON=93.85. The resulting (R+M)/2=96.28. The Hutson method clearly underestimated the RON octane values for this process.

The inventive catalyst produces very high octane alkylate even at the non-optimum conditions of high space velocity and low I/O ratio.

We claim as our invention:
1. An alkylation process comprising the steps of:
   a. contacting a mixture comprising isoparaffins and n-olefins with an acidic alkylation catalyst system comprising a transition alumina which has been previously contacted under substantially anhydrous conditions with a Lewis acid and with free Lewis acid under alkylation conditions to produce an alkylate stream, and
   b. separating the alkylate stream from the acidic alumina based alkylation catalyst.
2. The process of claim 1 where the transition alumina is selected from gamma-alumina, eta-alumina, theta-alumina, chi-alumina, rho-alumina, and mixtures.

3. The process of claim 2 where the transition alumina is selected from gamma-alumina, eta-alumina, and mixtures.

4. The process system of claim 1 where the strong Lewis acid is selected from $BF_3$, $BCl_3$, $BBr_3$, $BI_3$, $SbF_5$, $AlCl_3$, $AlBr_3$, $TiBr_4$, $TiCl_4$, $TiCl_3$, $ZrCl_4$, $PF_5$, $FeCl_3$, and $FeBr_3$.

5. The process system of claim 1 where the strong Lewis acid is selected from $SbF_5$, $AlCl_3$, and $BF_3$.

6. The process system of claim 5 where the strong Lewis acid is $BF_3$.

7. The process system of claim 2 where the strong Lewis acid is selected from $SbF_5$, $AlCl_3$, and $BF_3$.

8. The process system of claim 7 where the strong Lewis acid is $BF_3$.

9. The process system of claim 3 where the strong Lewis acid is selected from $SbF_5$, $AlCl_3$, and $BF_3$.

10. The catalyst system of claim 9 where the strong Lewis acid is $BF_3$.

11. The process of claim 4 where the alumina based alkylation catalyst additionally contains substantially no metals or semi-metals in catalytic amounts other than aluminum or boron.

12. The process of claim 1 where alkylation conditions include a temperature in the range of $-30°$ C. to $50°$ C.

13. The process of claim 1 where the mixture comprises 2-butene and isoparaffin.

14. The process of claim 1 where the contacting step is carried out in the substantial absence of isobutylene.

15. The process of claim 1 where the isoparaffin comprises isobutane.

16. The process of claim 13 where the isoparaffin comprises isobutane.

17. The process of claim 14 where the isoparaffin comprises isobutane.

18. The process of claim 1 where alkylation conditions include a WHSV between 0.5 to 30.0.

19. The process of claim 1 where the ratio of $C_4$–$C_{10}$ isoparaffins to $C_3$–$C_5$ olefins is in the range of one to 50.

20. The process of claim 1 including the step of mixing the alkylate stream with other hydrocarbons to produce a gasoline blending component or gasoline.

* * * * *